(12) United States Patent
Kelly et al.

(10) Patent No.: US 6,204,274 B1
(45) Date of Patent: Mar. 20, 2001

(54) INDOLYL DERIVATIVES AS SEROTONERGIC AGENTS

(75) Inventors: Michael G. Kelly, Plainsboro; Young H. Kang, Robbinsville, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/298,200

(22) Filed: Apr. 23, 1999

Related U.S. Application Data

(60) Provisional application No. 60/122,057, filed on Apr. 29, 1998.

(51) Int. Cl.[7] ............... A61K 31/445; C07D 401/00; C07D 421/00
(52) U.S. Cl. ............... 514/322; 514/323; 546/199; 546/201
(58) Field of Search ............... 514/322, 323; 546/199, 201

(56) References Cited

U.S. PATENT DOCUMENTS

| | | | |
|---|---|---|---|
| 5,342,845 | 8/1994 | Chokai et al. | 514/305 |
| 5,565,447 | 10/1996 | Forner et al. | 514/212 |
| 5,607,960 | 3/1997 | Wythes | 514/414 |
| 5,607,961 | 3/1997 | Cipollina et al. | 514/416 |
| 5,614,523 | 3/1997 | Audia et al. | 514/252 |
| 5,639,752 | 6/1997 | Macor | 514/374 |
| 5,639,772 | 6/1997 | Hammarberg et al. | 514/323 |
| 5,641,794 | 6/1997 | Booher et al. | 514/364 |
| 5,654,320 | 8/1997 | Catlow et al. | 514/322 |
| 5,654,324 | 8/1997 | Booher et al. | 514/397 |
| 5,670,511 | 9/1997 | Marz et al. | 514/290 |
| 5,693,655 | 12/1997 | Bottcher et al. | 514/323 |
| 5,708,008 | 1/1998 | Audia et al. | 514/374 |
| 5,792,763 | 8/1998 | Fritz et al. | 514/228.2 |

FOREIGN PATENT DOCUMENTS

| | | |
|---|---|---|
| 9533721 | 12/1995 | (WO) . |
| 9623784 | 8/1996 | (WO) . |
| 9828293 | 7/1998 | (WO) . |

OTHER PUBLICATIONS

Chemical Abstract vol. 98 No. 27343, Bondar et al, "Bio. Activity of Some Benzionidazole Derivatives" (1983).*
Gueremy et al., J. Med. Chem, 1980, 23, 1306–1310.
Malleron et al., J. Med. Chem., 1993, 36, 1194–1202.
Bergman, J. Heterocyclic Chem., 1970, 1071–1076.
Guillaume et al., Eur. J. Med. Chem., 1987, 22(1), 33–34.
Cheetham et al., Neuropharmacol. 32:737, 1993.
Cheng and Prusoff, Biochem. Pharmacol., 22, 3099, 1973.
Bowen et al., TINS, vol. 17, No. 4, 1994.
Freter et al., Arzneim.–Forsch. 35(1), 272–276, 1985.

* cited by examiner

*Primary Examiner*—John Kight
*Assistant Examiner*—Raymond Covington
(74) *Attorney, Agent, or Firm*—Steven R. Eck

(57) ABSTRACT

The present invention provides compounds of the formula (1):

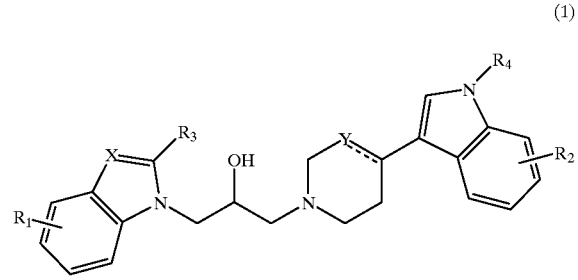

wherein
  $R_1$ and $R_2$ each independently represent hydrogen, hydroxy, F, Cl, Br, I, CN, 1 to 6 carbon alkyl, 1 to 6 carbon alkoxy, nitro, $CF_3$ and phenyloxy or benzyloxy, in which the aromatic ring can be optionally substituted by from 1 to 3 groups selected from $C_1$–$C_6$ alkoxy (preferably OMe), F, Cl, Br, I, and $CF_3$;
  $R_3$ and $R_4$ are each independently a hydrogen, a 1 to 6 carbon alkyl or a $CH_2Ph$ in which the phenyl ring can be optionally substituted by from 1 to 3 groups selected from $C_1$–$C_6$ alkoxy (preferably OMe), F, Cl, Br, I, and $CF_3$;
  Y is selected from $CH_2$ or CH and,
  X is selected from a group represented by N, $CR_3$, $CHR_3$, CHCH;
or a pharmaceutically acceptable salt thereof, as well as pharmaceutical compositions and methods of using the compounds to treat central nervous system disorders, such as depression, anxiety, drug withdrawal, eating and sexual disorders and other conditions for which serotonin reuptake inhibitors are used.

15 Claims, No Drawings

INDOLYL DERIVATIVES AS SEROTONERGIC AGENTS

This application claims the benefit of U.S. Provisional Application No. 60/122,057, which was converted from U.S. patent application Ser. No. 09/069,045, filed Apr. 29, 1998, pursuant to a petition filed under 37 C.F.R. 1.53(c)(2)(i).

This invention concerns a series of novel heteroaryl-β-hydroxypropylamines which are effective pharmaceuticals for the treatment of conditions related to or are affected by the reuptake of serotonin. The compounds are particularly useful for the treatment of depression, anxiety, drug withdrawal, eating and sexual disorders and other conditions for which serotonin reuptake inhibitors are used.

BACKGROUND TO THE INVENTION

In their article "4-(Indolyl-3)-1-(benzimidazolonylalkyl)-piperidines, a Novel Group of Potential Antiallergy Compounds", Arzneim.-Forsch, 35 (1), 272–276 (1985), Freter et al. disclose compounds of the formula:

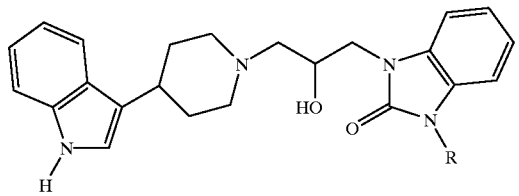

as anti-allergy agents by virtue of their histamine H1-blocking actions in addition to weak mast cell stabilizing properties.

SUMMARY OF THE INVENTION

Depression is a psychiatric condition thought to be associated with decreased serotonin release. Most antidepressant agents (e.g. fluoxetine) potentiate the effects of serotonin by blocking the termination of its activity through reuptake into nerve terminals. The present invention provides a series of novel indolyl derivatives which inhibit the reuptake of serotonin, to processes for their preparation, to pharmaceutical compositions containing them and to their use in therapy for the treatment of central nervous system disorders, particularly depression.

Compounds of the present invention are represented by the general formula (1):

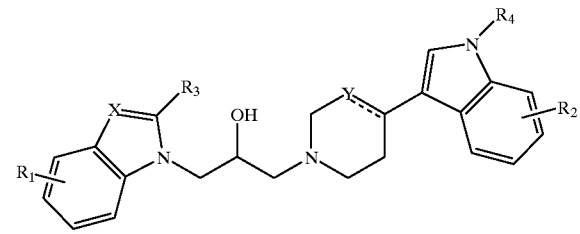

(1)

wherein:
$R_1$ and $R_2$ each independently represent hydrogen, hydroxy, F, Cl, Br, I, CN, 1 to 6 carbon alkyl, 1 to 6 carbon alkoxy, nitro, $CF_3$ and phenyloxy or benzyloxy, in which the aromatic ring can be optionally substituted by from 1 to 3 groups selected from $C_1$–$C_6$ alkoxy (preferably OMe), F, Cl, Br, I, and $CF_3$;

$R_3$ and $R_4$ are each independently a hydrogen, a 1 to 6 carbon alkyl or a $CH_2Ph$ in which the phenyl ring can be optionally substituted by from 1 to 3 groups selected from $C_1$–$C_6$ alkoxy (preferably OMe), F, Cl, Br, I, and $CF_3$;

Y is selected from $CH_2$ or CH and,

X is selected from a group represented by N, $CR_3$, $CHR_3$, CHCH;

or a pharmaceutically acceptable salt thereof.

A preferred group of compounds of this invention are those in which X is N and $R_1$, $R_2$, $R_3$, $R_4$ and Y are as defined above. Another preferred group herein comprises compounds wherein X is $CR_3$, $CHR_3$ or CHCH and $R_1$, $R_2$, $R_3$, $R_4$ and Y are as defined above.

The pharmaceutically acceptable salts are the acid addition salts which can be formed from a compound of the above general formula and a pharmaceutically acceptable inorganic acid such as phosphoric, sulfuric, hydrochloric, hydrobromic, citric, maleic, fumaric, acetic, lactic or methanesulfonic acid.

DETAILED DESCRIPTION OF THE INVENTION

Compounds of the present invention may be prepared using conventional methods. For example, treatment of the indole or benzimidazole derivative (2) with glycidyl tosylate affords the epoxide (3). Reaction of the epoxide with the piperidine or tetrahydropyridine derivatives (4) and (5) affords the respective products (1).

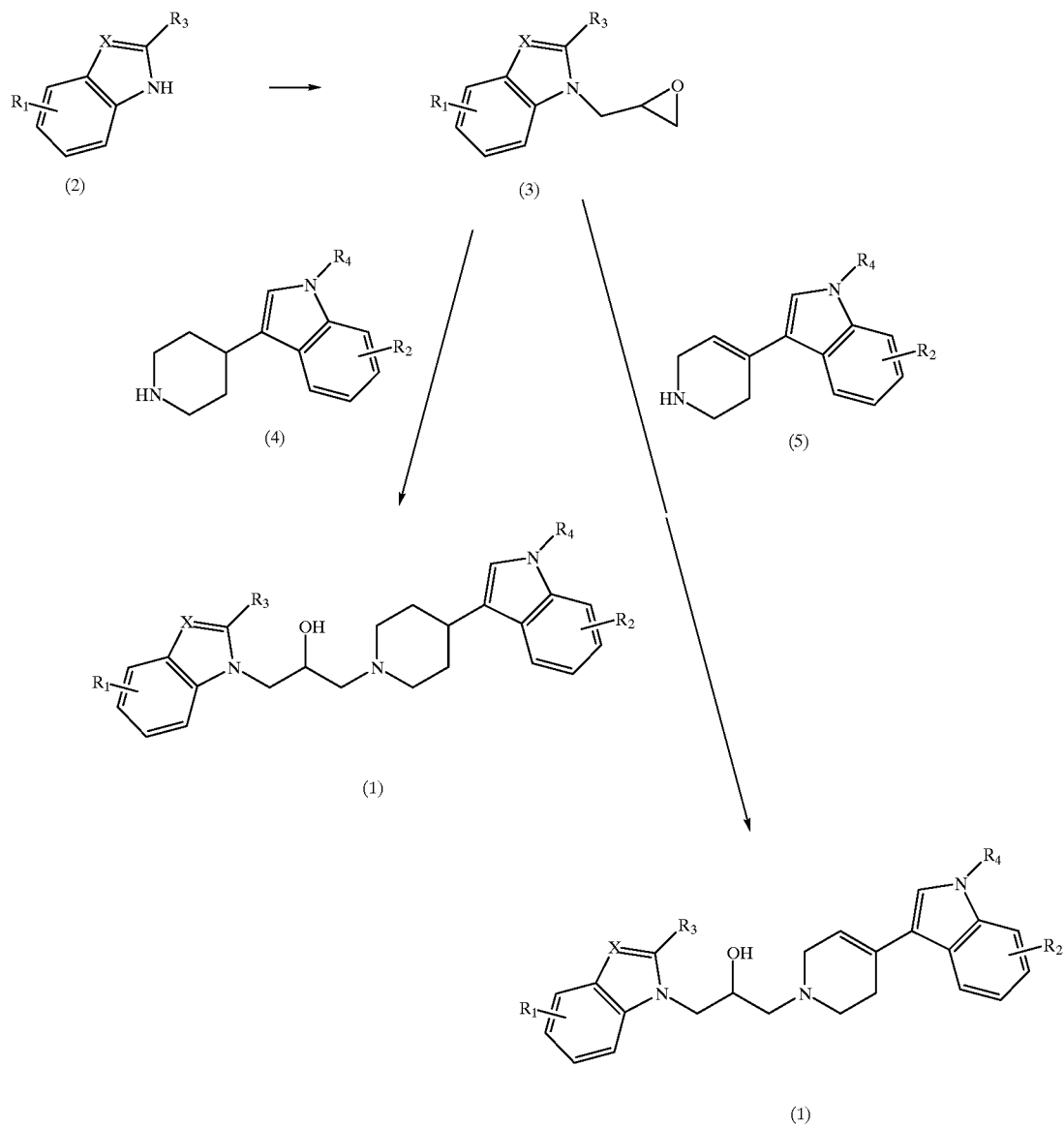

The preparation of the appropriately substituted 3-(4-piperidinyl)indoles and 3-(4-tetrahydro pyridinyl) indoles can be achieved by known and conventional methods. For example, the reaction of an optionally substituted indole with 4-piperidone affords the 3-(4-tetrahydropyridinyl) indole (5). This can be reduced using standard catalytic hydrogenation methodology to afford a 3-(4-piperidinyl) indole (4). Such methodology is described in C. Gueremy et al., J. Med. Chem., 1980, 23, 1306–1310, J-L. Malleron et al., J. Med. Chem., 1993, 36, 1194–1202 and J. Bergman, J. Heterocyclic. Chem., 1970, 1071–1076.

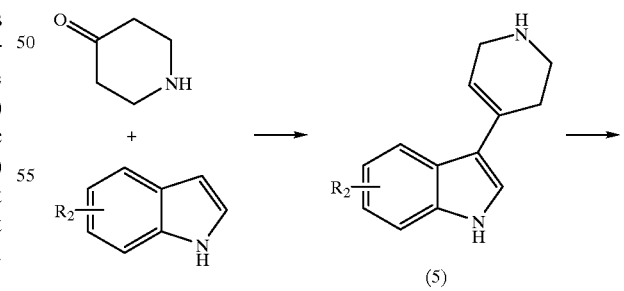

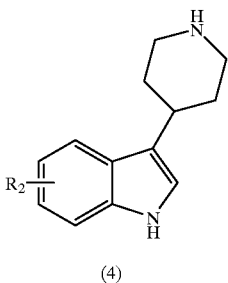

(4)

The present invention provides methods for inhibiting the reuptake of serotonin in mammals, preferably in humans. Compounds of the present invention inhibit with very high affinity the binding of paroxetine to the serotonin transporter, and consequently, they are useful for the treatment of central nervous system disorders such as depression, anxiety, including generalized anxiety disorder, sleep disorders, sexual dysfunction, obsessive-compulsive disorders, obesity, bulimia nervosa, migraine, chronic fatigue syndrome, pain, particularly neuropathic pain, panic disorder, post traumatic stress disorder, late luteal phase dysphoric disorder (also referred to a premenstrual syndrome), Tourette's syndrome, alcohol and cocaine addiction, Parkinson's disease, schizophrenia and for cognition enhancement such as in Alzheimer's disease.

It is understood that the therapeutically effective dosage to be used in the treatment of a specific psychosis must be subjectively determined by the attending physician. Variables involved include the specific psychosis or state of anxiety and the size, age and response pattern of the patient. The novel method of the invention for treating conditions related to or are affected by the reuptake of serotonin comprise administering to warm-blooded animals, including humans, an effective amount of at least one compound of this invention or a non-toxic, pharmaceutically acceptable addition salt thereof. The compounds may be administered orally, rectally, parenterally, or topically to the skin and mucosa. The usual daily dose is depending on the specific compound, method of treatment and condition treated. An effective dose of 0.01–1000 mg/Kg may be used for oral application, preferably 0.5–500 mg/Kg, and an effective amount of 0.1–100 mg/Kg may be used for parenteral application, preferably 0.5–50 mg/Kg. The therapeutically effective dosage to be used in the treatment of a specific psychosis must be subjectively determined by the attending physician. The variables involved include the specific malady or disorder and the size, age and response pattern of the patient.

The present invention also includes pharmaceutical compositions containing a compound of this invention, or a pharmaceutically acceptable salt thereof, and one or more pharmaceutically acceptable carriers or excipients. Applicable solid carriers or excipients can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The affinity of drugs for the serotonin transporter was determined by assessing the ability of agents to displace specifically bound 3H-paroxetine binding from rat cortical membranes. This procedure is a modification of that used by Cheetham et al., 1993 (Neuropharmacol. 32: 737–743, 1993). Nonspecific binding was determined using fluoxetine. Using this assay, the following Ki's were determined for a series of standard serotonin uptake inhibitors.

$^3$H-Paroxetine Binding to Assess Affinity of Drugs for the Serotonin Transporter A protocol similar to that used by Cheetham et al. (Neuropharmacol. 32: 737, 1993) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method of Cheng and Prusoff (Biochem. Pharmacol. 22: 3099, 1973); Ki=IC50/((Radioligand conc.)/(1+KD)).

| Compound | Inhibition of [3H]-Paroxetine binding Ki (nM) |
| --- | --- |
| Clomipramine | 0.18 |
| Fluoxetine | 4.42 |
| Imipramine | 17.6 |
| Zimelidine | 76.7 |

The results for a number of examples of compounds of formula (1) in this standard experimental test procedure were as follows:

| Compound | Inhibition of [3H]-Paroxetine binding Ki (nM) |
| --- | --- |
| Example 8 | 1.4 |
| Example 10 | 0.01 |
| Example 11 | 0.04 |
| Example 12 | 1.7 |
| Example 13 | 0.4 |
| Example 14 | 0.03 |
| Example 15 | 0.3 |

The following non-limiting specific examples are included to illustrate the synthetic procedures used for preparing compounds of the formula (1). In these examples, all chemicals and intermediates are either commercially available or can be prepared by standard procedures found in the literature or are known to those skilled in the art of organic synthesis.

EXAMPLE 1

1-N-Glycidyl-5-fluoro-indole

Epibromohydrin (1.4 ml, 16.5 mmole) was added to a stirred solution of 5-fluoroindole (2.0 g, 15 mmole) and sodium hydride (0.66 g, 16.5 mmole) in anhydrous DMF (20 ml), and the mixture was heated at 60° C. under nitrogen for 15 hours. Water (100 ml) was added and the product extracted into CH2Cl2 (3×35 ml). The combined organics were washed with water (25 ml), brine (25 ml) and dried over anhydrous sodium sulfate. Filtration and concentration in vacuo gave the crude product as a viscous yellow colored oil (2.7 g). This was purified by flash silica gel chromatography (30% ethyl acetate in hexane) to afford the titled product as a viscous oil (2.5 g, 89% yield).
Elemental Analysis for: C11H10FNO Calculated: C, 69.10; H, 5.27; N, 7.33 Found: C, 69.24; H, 5.67; N, 7.36

EXAMPLE 2

1-N-Glycidyl-4-methoxy-indole

Epibromohydrin (0.64 ml, 7.5 mmole) was added to a stirred solution of 4-methoxyindole (1.0 g, 6.8 mmole) and sodium hydride (0.3 g, 7.8 mmole) in anhydrous DMF (20 ml), and the mixture was heated at 60° C. under nitrogen for two hours. Water (100 ml) was added and the product extracted into CH2Cl2 (3×25 ml). The combined organics were washed with water (25 ml), brine (25 ml) and dried over anhydrous sodium sulfate. Filtration and concentration in vacuo gave the crude product as a yellow colored oil (1.5 g). This was purified by flash silica gel chromatography (30% ethyl acetate in hexane) to afford the titled product as a light oil (1.27 g, 92% yield).
Elemental Analysis for: C12H13NO2 Calculated: C, 70.92; H, 6.45; N, 6.89 Found: C, 71.05; H, 6.57; N, 6.96

EXAMPLE 3

1-N-Glycidyl-4-fluoro-indole

Epibromohydrin (0.64 ml, 7.5 mmole) was added to a stirred solution of 4-fluoroindole (1.0 g, 7.4 mmole) and sodium hydride (0.32 g, 8.1 mmole) in anhydrous DMF (20 ml), and the mixture was heated at 60° C. under nitrogen for 15 hours. Water (100 ml) was added and the product extracted into CH2Cl2 (3×25 ml). The combined organics were washed with water (25 ml), brine (25 ml) and dried over anhydrous sodium sulfate. Filtration and concentration in vacuo gave the crude product as a yellow colored oil (1.34 g). This was purified by flash silica gel chromatography (30% ethyl acetate in hexane) to afford the titled product as a light oil (1.27 g, 90% yield).
Elemental Analysis for: C11H10FNO Calculated: C, 69.10; H, 5.27; N, 7.33 Found: C, 69.24; H, 5.37; N, 7.46

EXAMPLE 4

1-N-Glycidyl-indole

Epibromohydrin (0.73 ml, 8.5 mmole) was added to a stirred solution of indole (1.0 g, 8.5 mmole) and sodium hydride (0.34 g, 8.5 mmole) in anhydrous DMF (20 ml), and the mixture was heated at 60° C. under nitrogen for two hours. Water (100 ml) was added and the product extracted into CH2Cl2 (3×25 ml). The combined organics were washed with water (25 ml), brine (25 ml) and dried over anhydrous sodium sulfate. Filtration and concentration in vacuo gave the crude product as a light yellow colored oil (1.45 g). This was purified by flash silica gel chromatography (30% ethyl acetate in hexane) to afford the titled product as a light oil (1.37 g, 93% yield).
Elemental Analysis for: C11H11NO Calculated: C, 76.27; H, 6.40; N, 8.09 Found: C, 76.24; H, 6.37; N, 8.06

EXAMPLE 5

1-N-(S)-Glycidyl-4-methoxyindole (2S)-(+)-Glycidyl tosylate (1.55 g, 6.8 mmole) was added to a stirred solution of 4-methoxyindole (1.0 g, 6.8 mmole), sodium hydride (0.3 g, 7.5 mmole) and 18-crown-6 (10 mg) in anhydrous DMF (20 ml), and the mixture was heated at 60° C. under nitrogen for five hours. Water (100 ml) was added and the product extracted into CH2Cl2 (3×25 ml). The combined organics were washed with water (25 ml), brine (25 ml) and dried over anhydrous sodium sulfate. Filtration and concentration in vacuo gave the crude product as a light yellow colored oil (1.15 g). This was purified by flash silica gel chromatography (30% ethyl acetate in hexane) to afford the titled product as a light oil (0.65 g, 47% yield).
Elemental Analysis for: C12H13NO2 Calculated: C, 70.92; H, 6.45; N, 6.89 Found: C, 71.11; H, 6.59; N, 6.99

EXAMPLE 6

1-N-(S)-Glycidyl-4-fluoroindole (2S)-(+)-Glycidyl tosylate (1.7 g, 7.4 mmole) was added to a stirred solution of 4-fluoroindole (1.0 g, 7.4 mmole), sodium hydride (0.33 g, 8.1 mmole) and 18-crown-6 (10 mg) in anhydrous DMF (20 ml), and the mixture was heated at 60° C. under nitrogen for five hours. Water (100 ml) was added and the product extracted into CH2Cl2 (3×25 ml). The combined organics were washed with water (25 ml), brine (25 ml) and dried over anhydrous sodium sulfate.

Filtration and concentration in vacuo gave the crude product as a light yellow colored oil (1.15 g). This was purified by flash silica gel chromatography (30% ethyl acetate in hexane) to afford the titled product as a light oil (0.4 g, 28% yield).

Elemental Analysis for: C11H10FNO Calculated: C, 69.10; H, 5.27; N, 7.33 Found: C, 69.27; H, 5.40; N, 7.43

EXAMPLE 7

1-N-Glycidyl-2-methylbenzimidazole

Epibromohydrin (1.0 g, 7.6 mmole) was added to a stirred solution of 2-methylbenzimidazole (1.0 g, 7.6 mmole) and sodium hydride (0.3 g, 7.6 mmole) in anhydrous DMF (20 ml), and the mixture was heated at 60° C. under nitrogen for 0.5 hours. Water (100 ml) was added and the product extracted into CH2Cl2 (3×25 ml). The combined organics were washed with water (25 ml), brine (25 ml) and dried over anhydrous sodium sulfate. Filtration and concentration in vacuo gave the crude product as a light yellow colored oil (1.4 g). This was purified by flash silica gel chromatography (10% methanol in CH2Cl2) to afford the titled product as a light oil (0.64 g, 45% yield).

Elemental Analysis for: C11H12N2O Calculated: C, 70.19; H, 6.43; N, 14.88 Found: C, 70.24; H, 6.47; N, 14.98

EXAMPLE 8

1-(5-Fluoro-indol-1-yl)-3-[4-(1H-indol-3-yl)-3,6-dihydro-2H-pyridin-1-yl]-propan-2-ol A methanolic solution of 1-N-glycidyl-5-fluoroindole (0.52 g, 3.0 mmole) from example 1 and 3-(4-tetrahydropyridinyl)indole (0.59 g, 3.0 mmole) was refluxed under nitrogen for 15 hours. The reaction mixture was concentrated in vacuo and the product purified by flash silica gel chromatography (ethyl acetate) to afford the titled compound as a light yellow colored solid (0.91 g, 78% yield). Treatment with a 0.25 M ethanolic solution of fumaric acid (0.5 equivalents) gave the required salt as a yellow colored solid. The product was recrystallized from ethanol.

mp 206–207° C.

Elemental Analysis for: C24H24FN3O 0.5C4H4O4 Calculated: C, 69.78; H, 5.86; N, 9.39 Found: C, 69.46; H, 5.71; N, 9.21

EXAMPLE 9

1-(5-Fluoro-indol-1-yl)-3-[4-(1H-indol-3-yl)-piperidin-1-yl]-propan-2-ol

A methanolic solution of 1-N-glycidyl-5-fluoroindole (0.52 g, 3.0 mmole) from example 1 and 3-(4-piperidinyl) indole (0.6 g, 3.0 mmole) was refluxed under nitrogen for 15 hours. The reaction mixture was concentrated in vacuo and the product purified by flash silica gel chromatography (ethyl acetate) to afford the titled compound as an oil (0.599 g, 50% yield). Treatment with a 0.25 M ethanolic solution of fumaric acid (0.5 equivalents) gave the required product as a white solid. The product was recrystallized twice from ethanol.

mp 215–216° C. Elemental Analysis for: C24H26FN3O 0.5C4H4O4 0.8CH2Cl2 Calculated: C, 68.65; H, 6.22; N, 9.21 Found: C, 68.44; H, 6.36; N, 9.14

EXAMPLE 10

1-(4-Fluoro-indol-1-yl)-3-[4-(1H-indol-3-yl)-3,6-dihydro-2H-pyridin-1-yl]-propan-2-ol A methanolic solution of 1-N-glycidyl-4-fluoroindole (0.52 g, 3.0 mmole) from example 3 and 3-(4-tetrahydropyridinyl)indole (0.59 g, 3.0 mmole) was refluxed under nitrogen for 15 hours. The reaction mixture was concentrated in vacuo and the product purified by flash silica gel chromatography (ethyl acetate) to afford the titled compound as a pale yellow colored solid (0.61 g, 53% yield). Treatment with a 0.25M ethanolic solution of fumaric acid (0.5 equivalents) gave the required product as a yellow colored solid. The product was recrystallized from ethanol. mp 136–137° C. Elemental Analysis for: C24H24FN3O 0.5C4H4O4 0.12H2O 0.3EtOH Calculated: C, 68.93; H, 6.10; N, 9.07 Found: C, 68.58; H, 6.17; N, 8.82

EXAMPLE 11

1-[4-(1H-Indol-3-yl)-3,6-dihydro-2H-pyridin-1-yl]-3-(4-methoxy-indol-1-yl)-propan-2-ol A methanolic solution of 1-N-glycidyl-4-methoxyindole (0.6 g, 3.0 mmole) from example 2 and 3-(4-tetrahydropyridinyl)indole (0.59 g, 3.0 mmole) was refluxed under nitrogen for 15 hours. The reaction mixture was concentrated in vacuo and the product purified by flash silica gel chromatography (ethyl acetate) to afford the titled compound as a yellow colored solid (0.73 g, 60% yield). Treatment with a 0.25M ethanolic solution of fumaric acid (0.5 equivalents) gave the required product as a yellow colored solid. The product was recrystallized from ethanol. mp 140–143° C. Elemental Analysis for: C25H27N3O2 0.5C4H4O4 0.17H2O Calculated: C, 70.10; H, 6.39; N, 9.08 Found: C, 69.70; H, 6.27; N, 8.93

EXAMPLE 12

1-Indol-1-yl-3-[4-(1H-indol-3-yl)-3,6-dihydro-2H-pyridin-1-yl]-propan-2-ol

A methanolic solution of 1-N-glycidylindole (0.52 g, 3.0 mmole) from example 4 and 3-(4-tetrahydropyridinyl)indole (0.59 g, 3.0 mmole) was refluxed under nitrogen for 24 hours. The reaction mixture was concentrated in vacuo and the product purified by flash silica gel chromatography (ethyl acetate) to afford the titled compound as a yellow colored solid (0.53 g, 47% yield). Treatment with a 0.25M ethanolic solution of fumaric acid (0.5 equivalents) gave the required product as a yellow colored solid. The product was recrystallized from ethanol.

mp 209–210° C. Elemental Analysis for: C24H25N3O2 0.5C4H4O4 Calculated: C, 72.71; H, 6.34; N, 9.78 Found: C, 72.72; H, 6.49; N, 9.62

EXAMPLE 13

1-[4-(1H-Indol-3-yl)-3,6-dihydro-2H-pyridin-1-yl]-3-(2-methyl-benzoimidazol-1-yl)-propan-2-ol A methanolic solution of 1-N-glycidyl-2-methylbenzimidazole (0.64 g, 3.4 mmole) from example 7 and 3-(4-tetrahydropyridinyl)indole (0.67 g, 3.4 mmole) was refluxed under nitrogen for 24 hours. The reaction mixture was concentrated in vacuo and the product purified by flash silica gel chromatography (10% methanol in ethyl acetate) to afford the titled compound as a pale yellow colored solid (0.11 g, 9% yield). Treatment with a 0.25M ethanolic solution of fumaric acid (0.5 equivalents) gave the required product as a yellow colored solid. The product was recrystallized from ethanol.

mp 206–208° C. Elemental Analysis for: C24H26N4O 0.5C4H4O4 1.5H2O Calculated: C, 66.22; H, 6.63; N, 11.88 Found: C, 66.29; H, 6.20; N, 11.73

EXAMPLE 14

(2S)-1-[4-(1H-Indol-3-yl)-3,6-dihydro-2H-pyridin-1-yl]-3-(4-methoxy-indol-1-yl)-propan-2-ol A methanolic solution of 1-N-(S)-glycidyl-4-methoxyindole (0.65 g, 3.2 mmole) from example 5 and 3-(4-tetrahydropyridinyl)indole (0.63 g, 3.2 mmole) was refluxed under nitrogen for 24 hours. The reaction mixture was concentrated in vacuo and the product purified by flash silica gel chromatography (10% hexane in ethyl acetate) to afford the titled compound as a pale yellow colored solid (0.6 g, 47% yield). Treatment with a 0.25M ethanolic solution of fumaric acid (0.5 equivalents) gave the required product as a yellow colored solid. The product was recrystallized from ethanol.

mp 155–158° C. Elemental Analysis for: C25H27N3O2 0.5C4H4O4 1H2O Calculated: C, 67.91; H, 6.54; N, 8.80 Found: C, 67.81; H, 6.31; N, 8.50

EXAMPLE 15

(2S)-1-(4-Fluoro-indol-1-yl)-3-[4-(1H-indol-3-yl)-3,6-dihydro-2H-pyridin-1-yl]-propan-2-ol A methanolic solution of 1-N-(S)-glycidyl-4-fluoroindole (0.396 g, 2.3 mmole) from example 6 and 3-(4-tetrahydropyridinyl)indole (0.46 g, 2.3 mmole) was refluxed under nitrogen for 24 hours. The reaction mixture was concentrated in vacuo and the product purified by flash silica gel chromatography (10% hexane in ethyl acetate) to afford the titled compound as a pale yellow colored solid (0.44 g, 48% yield). Treatment with a 0.25M ethanolic solution of fumaric acid (0.5 equivalents) gave the required product as a yellow colored solid. The product was recrystallized from ethanol.

mp 135–136° C. Elemental Analysis for: C24H24FN3O 0.5C4H4O4 0.5H2O 0.32EtOH Calculated: C, 67.90; H, 6.19; N, 8.92 Found: C, 68.08; H, 6.10; N, 8.76

What is claimed:

1. A compound according to Formula (1):

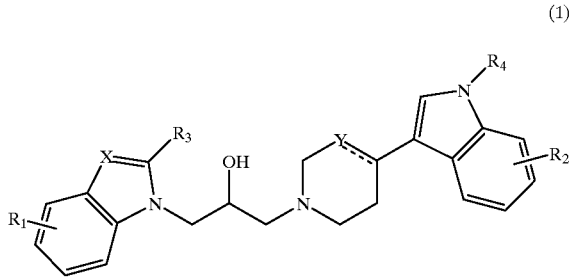

(1)

wherein:

$R_1$ and $R_2$ each independently represent hydrogen, hydroxy, F, Cl, Br, I, CN, 1 to 6 carbon alkyl, 1 to 6 carbon alkoxy, nitro, $CF_3$ and phenyloxy or benzyloxy, in which the aromatic ring can be optionally substituted by from 1 to 3 groups selected from $C_1$–$C_6$ alkoxy, F, Cl, Br, I, and $CF_3$;

$R_3$ and $R_4$ are each independently a hydrogen, a 1 to 6 carbon alkyl or a $CH_2Ph$ in which the phenyl ring can be optionally substituted by from 1 to 3 groups selected from $C_1$–$C_6$ alkoxy (preferably OMe), F, Cl, Br, I, and $CF_3$;

Y is selected from $CH_2$ or CH and,

X is selected from a group represented by N, $CR_3$, $CHR_3$, CHCH;

or a pharmaceutically acceptable salt thereof.

2. A compound of claim 1 which is 1-(5-fluoro-indol-1-yl)-3-[4-(1H-indol-3-yl)-3,6-dihydro-2H-pyridin-1-yl]-propan-2-ol, or a pharmaceutically acceptable salt thereof.

3. A compound of claim 1 which is 1-(5-fluoro-indol-1-yl)-3-[4-(1H-indol-3-yl)-piperidin-1-yl]-propan-2-ol, or a pharmaceutically acceptable salt thereof.

4. A compound of claim 1 which is 1-(5-fluoro-indol-1-yl)-3-[4-(1H-indol-4-yl)-piperazin-1-yl]-propan-2-ol, or a pharmaceutically acceptable salt thereof.

5. A compound of claim 1 which is 1-{1-[3-(5-fluoro-indol-1-yl)-2-hydroxy-propyl]-piperidin-4-yl}-1,3-dihydro-benzoimidazol-2-one, or a pharmaceutically acceptable salt thereof.

6. A compound of claim 1 which is 1-(4-fluoro-indol-1-yl)-3-[4-(1H-indol-3-yl)-3,6-dihydro-2H-pyridin-1-yl]-propan-2-ol, or a pharmaceutically acceptable salt thereof.

7. A compound of claim 1 which is 1-[4-(1H-indol-3-yl)-3,6-dihydro-2H-pyridin-1-yl]-3-(4-methoxy-indol-1-yl)-propan-2-ol, or a pharmaceutically acceptable salt thereof.

8. A compound of claim 1 which is 1-indol-1-yl-3-[4-(1H-indol-3-yl)-3,6-dihydro-2H-pyridin-1-yl]-propan-2-ol, or a pharmaceutically acceptable salt thereof.

9. A compound of claim 1 which is 1-[4-(1H-indol-3-yl)-3,6-dihydro-2H-pyridin-1-yl]-3-(2-methyl-benzoimidazol-1-yl)-propan-2-ol, or a pharmaceutically acceptable salt thereof.

10. A compound of claim 1 which is (2S)-1-[4-(1H-indol-3-yl)-3,6-dihydro-2H-pyridin-1-yl]-3-(4-methoxy-indol-1-yl)-propan-2-ol, or a pharmaceutically acceptable salt thereof.

11. A compound of claim 1 which is (2S)-1-(4-fluoro-indol-1-yl)-3-[4-(1H-indol-3-yl)-3,6-dihydro-2H-pyridin-1-yl]-propan-2-ol, or a pharmaceutically acceptable salt thereof.

12. A pharmaceutical composition comprising a pharmaceutically acceptable carrier or excipient and a compound of claim 1, or a pharmaceutically acceptable salt thereof.

13. A method for inhibiting the reuptake of serotonin in a mammal, the method comprising administering to the mammal in need thereof an effective amount of a compound of claim 1, or a pharmaceutically acceptable salt thereof.

14. A method of treating depression in a mammal, the method comprising administering to the mammal in need thereof an effective amount of a compound of claim 1, or a pharmaceutically acceptable salt thereof.

15. A method of treating anxiety in a mammal, the method comprising administering to the mammal in need thereof an effective amount of a compound of claim 1, or a pharmaceutically acceptable salt thereof.

* * * * *